US009968773B1

(12) United States Patent
Hocking

(10) Patent No.: US 9,968,773 B1
(45) Date of Patent: *May 15, 2018

(54) METHOD AND SYSTEM FOR REHABILITATION OF SCAR TISSUE

(71) Applicant: Bruce Hocking, Toronto (CA)

(72) Inventor: Bruce Hocking, Toronto (CA)

(73) Assignee: Center for Pain and Stress Research, Ltd, Toronto (CA)

( * ) Notice: Subject to any disclaimer, the term of this patent is extended or adjusted under 35 U.S.C. 154(b) by 377 days.

This patent is subject to a terminal disclaimer.

(21) Appl. No.: 14/740,857

(22) Filed: Jun. 16, 2015

(51) Int. Cl.
*A61N 1/04* (2006.01)

(52) U.S. Cl.
CPC ................... *A61N 1/0464* (2013.01)

(58) Field of Classification Search
CPC .................................................. A61N 1/0464
USPC ........................................................ 607/115
See application file for complete search history.

(56) References Cited

U.S. PATENT DOCUMENTS

2014/0194949 A1* 7/2014 Wichner ............ A61N 1/36003
607/48

* cited by examiner

*Primary Examiner* — Christopher D Koharski
*Assistant Examiner* — Roland Dinga
(74) *Attorney, Agent, or Firm* — Clifford H. Kraft

(57) ABSTRACT

A method using a prior art hand-held device known as the Dolphin Neurostim™ to supply minute, concentrated micro-current impulses to the (outside) perimeters of scar tissue for the purpose of tissue diagnosis (through ohm resistance measurement), promotion of scar tissue repair (through electrical repolarization), and pain management (through sympathetic deregulation of the Autonomic Nervous System. The micro-current stimulus (therapy) is delivered through a tiny metallic spring tip (probe) ideally suited for location (detection) of specific treatment points (which have the cellular characteristic and lowered skin resistance). The device is activated to deliver a concentrated (DC) micro-current stimulus through the scar/suture tissue to another identical device located (mirrored) on the opposing side of the scar/suture. This stimulation reactivates cellular metabolism and membrane exchange, changing scars appearance, softening scar/suture tissue by releasing relating adhesions which re-balances the autonomic nervous system.

18 Claims, 26 Drawing Sheets

Four Stages of Scar Formation

Injury/cut

Blot Clotting

Scab Forms

Scar Forms

Four Stages of Scar Formation

Injury/cut

Blot Clotting

Scab Forms

Scar Forms

View of Adhesion Formation after scar formation on uterus

Uterus with no adhesions

Uterus with adhesions

View of Adhesion Formation after scar formation in muscle tissue

Muscle fibers with no adhesions

Muscle fibers with adhesions

Electrical Polarity of Normal Skin

Electrical Polarity of Skin after scar formation

Application methodology and electrical polarity of devices during St 36 Adhesion Release-SRT MPS Method Patient positioning, device placement and electrical polarity of devices during St 36 Adhesion Release-SRT MPS Method Application methodology and electrical polarity of devices during Sp 6 Electrical Reconnection-SRT MPS Method Patient positioning, device placement and electrical polarity of devices during
Sp 6 Electrical Reconnection-SRT MPS Method Sets forth a view of patient for
Internal Adhesion Release - SRT MPS Method-Gv 4

Abdominal Adhesion
Release-Circumvent scar

Gv 4 - Internal Adhesion
Release

B 25 - Internal Adhesion
Release

Sets forth a view of patient positioning for
Vagus Nerve Release - SRT MPS Method -Gb 12

Gb 12 - Vagus Nerve Tone

Abdominal Adhesion
Release-Circumvent scar

METHOD AND SYSTEM FOR REHABILITATION OF SCAR TISSUE

BACKGROUND

Field of Invention

The present invention relates generally to medical procedures and more particularly to the sequential application of micro-current therapy for the purpose of diagnosis and treatment of both surgical and traumatically formed scar and adhesion tissue.

Description of the Prior Art

The application of electrotherapy has been an accepted world-wide medical practice throughout the modern history of mankind. Electrotherapy has been applied for the purpose of wound and bone healing, pain and stress management. Micro-current parameters have been clinically proven to closely approximate the naturally occurring bio-electric currents in the body and therefore more effectively influencing the body's tissue healing and repair. Research has shown that tiny Micro-current impulses enhance three variables critical to healing: ATP (adenosine triphosphate), Protein synthesis, and Cellular Membrane transport. The same research shows that stronger AC Milliamperage (TENS) inhibits the same cellular healing process.

Microcurrent Point Stimulation appears to provide the strongest enhancement of cellular membrane transport through its unique ability to concentrate and focus high density micro-current stimulation directly through diseased scar tissue through a unique application approach. This unique process of simultaneous dual application of negative poled current from one tiny tip through scar tissue into a second other tiny tip forces a negative poled current directly through the scar in an electrical sewing needle approach, which is necessary for scar tissue cellular change. This novel approach of MPS application quickly changes the bio-electric voltage potentials across scar cell membranes, allowing for increased cellular metabolism and reversal of scar tissue polarity, which is the key to scar release.

Scars are formed by traumatic injury or surgical procedures or repeated micro-trauma such as over-training or repetitive stress injuries. When these events occur, special cells called fibroblasts form a wound matrix and secrete collagen to initiate tissue healing. The wound matrix, initially soft, quickly stiffens and pulls the edges of the wound concentrically inwards as the tissues heals, forming "scabs". As the scabs heal, they harden and form scars. The body responds to scar formation by internally growing fibrous adhesions underneath the scar, which is an unavoidable by-product of the healing process.

Adhesions develop as the body attempts to repair itself. They are fibrous bands that form between tissues and organs, often as a result of scars due to injury or surgery. They may be thought of as internal scar tissue that connect tissues that are not normally connected. These bands of scar-like tissue that form between two surfaces inside the body and cause them to stick together. Problems may occur if the adhesions cause an organ or body part to: twist, be pulled out of position, or be able to move normally. The adhesive tissue also forms in soft tissue areas of the human body, such as muscles, tendons, and ligaments. As scar tissue builds up, it prevents the muscles, tendons, and ligaments from lengthening and contracting, thereby resulting in lost range of motion, pain, and decreased stability. In addition, the build-up of adhesive tissue generally causes pain and dysfunction in the surrounding areas of the affected joints, organs and tissues, producing chronic symptoms that last much longer than the injury itself.

As adhesion tissue builds up, they also strain fascia creating kinks and irregularities within the body wide fascial system by pulling fascia inward towards the scar. These fascial strains prevent the muscles, tendons, and ligaments from naturally lengthening and contracting, resulting in lost range of motion. More importantly, these fascial strains produce further muscle imbalances and skeletal asymmetries, which accelerate joint degeneration (arthritis), nerve compression, and up-regulation of the Autonomic Nervous System.

During the scar healing phase, scar tissue also become electrically differentiated from the surrounding tissue. It is well known that cells, vessels, muscles and other body parts have a normal bio-electrical charge. Electrolytes usually pass freely into or out of the membranes and walls. During an injury, surgery or other cellular trauma, the membrane is broken and local bio-chemical transport is disrupted, accumulating cellular toxins. This action combined with the formation of thickened wound matrix, and no blood supply, creates a reversal of the normal bio-electrical state of the scar tissue, reversing it from a negative to a positive poled tissue. This scar tissue pole reversal produces electro-cellular instability in surrounding cells and the cells they are connected to.

These unstable electro-cellular signals are then sent outwards, resulting in a chain reaction of abnormal cellular miscommunication, often producing changes throughout the entire Autonomic Nervous System. The Autonomic Nervous System influences every nerve, vessel, organ, cell, or muscle in the body, controlling pain and any nervous dysfunction. Scars producing these instable cellular electrical changes are called interference sources, and their areas of cellular electrical instability influence are called interference patterns. It is theorized interference patterns have strong influence on the location of adhesion development.

Extensive clinical trials have demonstrated that the sequential bilateral application of micro-current stimulation at a low amplitude, low frequency and a square waveform produces the most pronounced cellular tissue changes and strongest functional changes within the nervous system. The primary goals of this new technique is to electrically repolarize positively poled scar tissue with negatively poled current in order to produce bio-cellular change to the scar and adhesive tissue. This new approach to scar release is called Scar Release Therapy-MPS Method (SRT-MPS Method).

Trials outcomes support the cellular benefits of MPS-SRT to include the reduction of the size, shape, and cosmetic texture of scar tissue by cellular re-polarization (changing scar cells from a positive to negative). This new therapeutic approach significantly improves cosmetic appearance of scars while simultaneously promoting cellular metabolism, reduced fascial strain and balance of the autonomic nervous system. This electrical balancing of the patient's autonomic nervous system and skin tissues can often produce long term and significant functional changes.

The cellular electrical rebalancing of scar tissues and the subsequent reverberations throughout the fascial, skeletal, nervous and endocrine systems is exceptionally powerful and is considered medically significant.

SUMMARY OF INVENTION

The present invention relates to the use of a prior art hand-held device known as the Dolphin Neurostim™ manufactured and supplied by Acumed Ltd. of Toronto Canada to supply minute, concentrated micro-current impulses to the (outside) perimeters of scar tissue (scars) for the purpose of tissue diagnosis (through ohm resistance measurement), promotion of scar tissue repair (through electrical repolarization), and pain management (through sympathetic deregulation of the Autonomic Nervous System The micro-current stimulus (therapy) is delivered through a tiny metallic spring tip (probe) ideally suited for location (detection) of specific treatment points (which have the cellular characteristic and lowered skin resistance). The device concurrently detects, measures, and stimulates treatment points located beside scar (tissue) and sutures. Once detected, the device is activated to deliver a concentrated (DC) micro-current stimulus through the scar/suture tissue to another identical device located (mirrored) on the opposing side of the scar/suture. This unique stimulation, when applied as described in this invention, reactivates cellular metabolism and membrane exchange, changing scars appearance, softening scar/suture tissue by releasing relating adhesions which re-balances the autonomic nervous system The present invention provides a methodology for effectively treating scar tissue throughout the body for both cosmetic improvement and health related benefits. This present invention is directed to a device and system of treatment using micro-current point stimulation called the SRT-MPS METHOD. The SRT-MPS METHOD is summarized as the simultaneous bilateral application of concentrated low-level micro-current to a scar's circumference for the purpose of tissue repair and pain management through sympathetic deregulation. The SRT-MPS METHOD of application can provide safe, immediate cellular change with residual benefits and is within the scope of practice of all therapists who are licensed to apply electro-therapy to patients.

DESCRIPTION OF THE FIGURES

Several drawings are now presented to illustrate features of the present invention:

FIG. (1) Sets forth topical view of scars four stages of healing.

FIG. (2) Sets forth a view of the formation of internal uterus adhesions after scar formation.

FIG. (3) Sets forth a view of the formation of muscle adhesions after scar/trauma formation.

FIG. (4) Sets forth a view of fascial pulling inward to center of topical scar.

FIG. (5) Sets forth a view of fascial "kink" pulling straining body-wide fascial system.

FIG. (6) Sets forth a view of electrical polarity of health skin.

FIG. (7) Sets forth a view of electrical polarity of skin after forming scar tissue.

FIG. (8) Sets forth a view of electrical polarity of skin and current during SRT-MPS application.

FIG. (9) Sets forth a view of electrical polarity of skin after SRT-MPS application.

FIG. (10) Sets forth a top overview of electrical polarity of skin and current during SRT-MPS application.

FIG. (11) Sets forth a top overview of application methodology and electrical polarity of devices during SRT-MPS para-scar treatment.

FIG. (12) Sets forth a top overview of application methodology and electrical polarity of devices during SRT-MPS opposite end treatment.

FIG. (13) Sets forth a top overview of application methodology and electrical polarity of devices during Fascia Release-SRT MPS Method.

FIG. (14) Sets forth a view of patient positioning, application methodology and electrical polarity of devices during Fascia Release-SRT MPS Method.

FIG. (15) Sets forth a top overview of application methodology and electrical polarity of devices during Adhesion Release-SRT MPS Method.

FIG. (16) Sets forth a view of patient positioning, application methodology and electrical polarity of devices during Adhesion Release-SRT MPS Method.

FIG. (17) Sets forth a top overview of application methodology and electrical polarity of devices during Electrical Reconnection-SRT MPS Method.

FIG. (18) Sets forth a view of patient positioning, application methodology and electrical polarity of devices during Electrical Reconnection-SRT MPS Method.

FIG. (19) Sets forth a top overview of application methodology and electrical polarity of devices during Emotional Broken Heart Release-SRT MPS Method.

FIG. (20) Sets forth a top overview of application methodology and electrical polarity of devices during Emotional Anxiety Release-SRT MPS Method.

FIG. (21) Sets forth a top overview of application methodology and electrical polarity of devices during Emotional Grief Release-SRT MPS Method.

FIG. (22) Sets forth a top overview of application methodology and electrical polarity of devices during Emotional Anger Release-SRT MPS Method.

FIG. (23) Sets forth a top overview of application methodology and electrical polarity of devices during Emotional Worry Release-SRT MPS Method.

FIG. (24) Sets forth a top overview of application methodology and electrical polarity of devices during Emotional Fear Release-SRT MPS Method.

Figure 26:
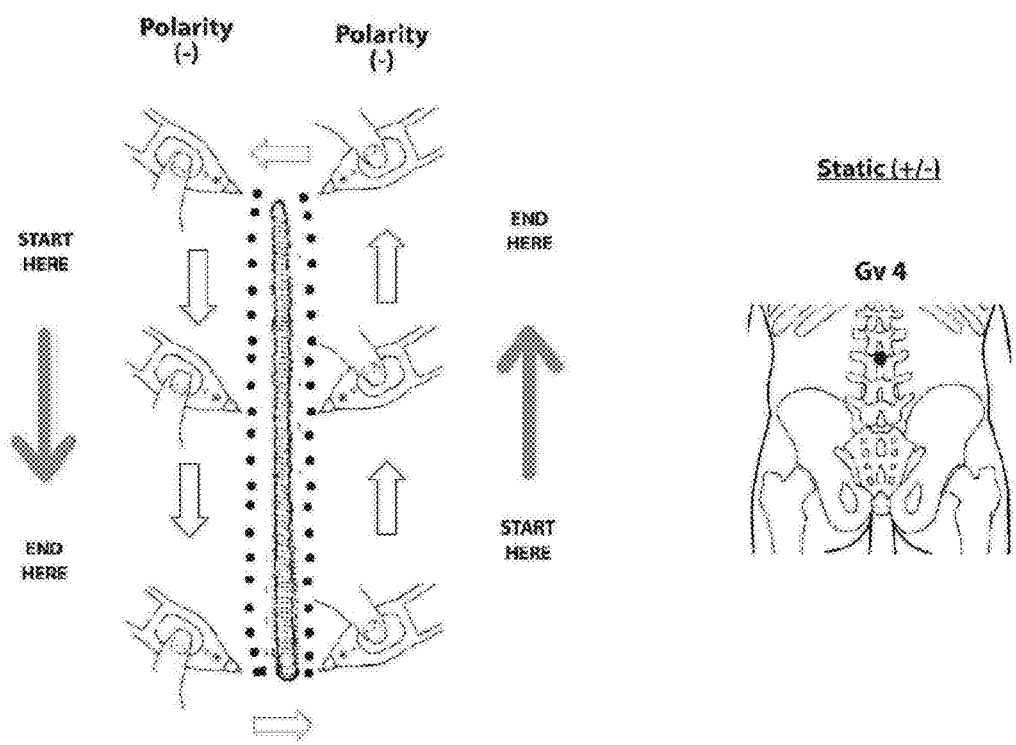
Figure 27:
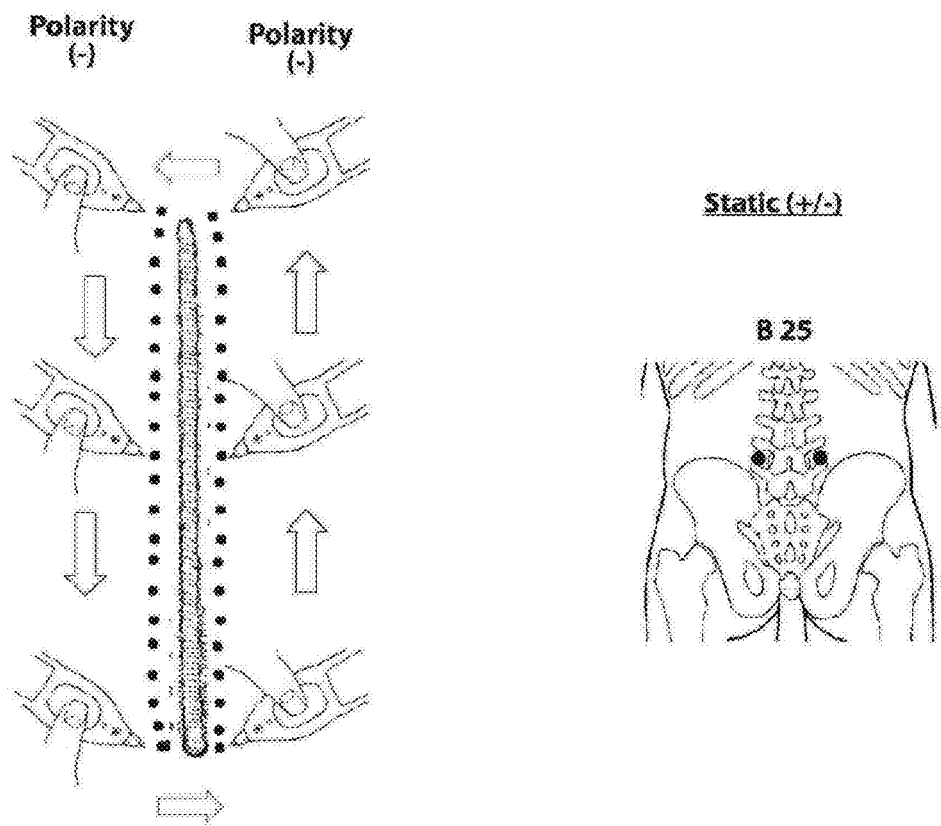

FIG. (25) Sets forth a view of patient positioning for Internal Adhesion Release-MPS Method used in FIGS. 26 and 27.

FIG. (26) Sets forth a top overview of application methodology and electrical polarity of devices during Internal Adhesions Release-SRT MPS Method-Gv 4.

FIG. (27) Sets forth application methodology and electrical polarity of devices during Adhesions Release-SRT MPS Method-B25.

FIG. (28) Sets forth a view of patient positioning for Vagus Nerve Release-SRT MPS Method-Vagus Nerve.

FIG. (29) Sets forth application methodology and electrical polarity of devices during Vagus Nerve Release-SRT MPS Method-Vagus Nerve.

FIG. (30) Sets forth a view of application methodology and electrical polarity of devices during Autonomic Nervous system Balance-SRT MPS Method.

FIG. (31) Sets forth a front and back view of the present invention therapeutic device, illustrating polarity setting.

Several drawings and illustrations have been presented to aid in understanding the present invention. The scope of the present invention is not limited to what is shown in the figures.

DESCRIPTION OF THE PREFERRED EMBODIMENTS

The prior art device used with the present invention produces a monophasic DC square wave which can be modified in application for enhanced outcomes in scar tissue release treatment. Since the scar itself is positive poled, forcing a negative poled current through the scar is imperative for healing tissue. Traditional pads application of electrotherapy is ineffective as application of current is too diffused and merely passes underneath the scars without any positive tissue influence. Manual therapies cannot electrically reverse scar cell polarity or enhance localized metabolism. However, forcing concentrated micro-current stimulation directly through the scar with a dual coordinated electrical approach is a highly effective methodology of reversing scar cell polarity and increasing cellular metabolism.

The present invention involves the simultaneous, targeted para-scar application of two prior art Dolphin Neurostims™ devices at the approximate location and intervals as surgical stitching. On one side of the scar, the first hand-held device is pre-programmed to a negative polarity setting. Mirrored on the other side of the scar, the second opposing hand-held device is pre-programmed to the bipolar (+/−) or balancing setting.

The technique of the simultaneous cathode (−ve) and pulsed cathode/anode (+/−) micro-current application forces (pushes) negative poled electrical current back and forth through the positively poled scar tissue similar to an electrical surgical stitching. The entire length of the scar is treated using this sequential application. This technique quickly repolarizes the positively charged scar tissue back into negatively charged "healthy" tissue, a process which is often visible to naked eye immediately after application. The technique is repeated throughout the entire circumference of the scar with the placement of the hand-held devices during application being mirrored opposite to each other on the scar to optimize (maximize) scar tissue change.

An important part of the present invention is the application process which integrates the dual application of micro-current applied to each side of the scar or adhesion along its entire length. This process also includes integration of the scar with key acupuncture points that enhance facial/adhesion release and electrical reconnection within the nervous system. The unique electrical parameters and method of delivery are other important parts of the present invention.

The present invention is used to treat scar tissue resulting from trauma or surgery. After the treatment, there are no physical limitations imposed allowing the patient to immediately resume normal daily activities. The treatment technique is simple to learn and may be easily and safely applied to others with a minimal amount of training. During application, patients report a slight tingling sensation followed by an overall feeling of relaxation and wellness.

The technique is applied with a patient prone or supine with two units being simultaneously engaged around the perimeter of the scar. The engagement (treatment) requires the applicator (therapist) to locate Therapeutically Active Points (TAP's) (skin areas beside the scar with lowered electrical resistance) and then initiate the activation phase which forces (pushes) the negatively poled current through the positively poled scar tissue. During activation phase, patients perceive a slight tingling sensation which is not uncomfortable or irritating.

The application of technique may be integrated with other therapies recommended by physician or therapist and will not interfere or produce adverse responses with any known medications.

Method of Treatment SRT-MPS-Method (SRT-MPS Method Application Methodology)

The present invention provides a methodology for effectively treating scar tissue throughout the body for cosmetic improvement and health related benefits. The outcomes produced using the unique application methodology of bilateral, negative poled, (focused) concentrated micro-current stimulation, at a cellular influencing low frequency and amplitudes can be impressive. Applying this stimulation in the following manner can often produce significant sympathetic deregulation and visible and palpable scar tissue changes within one application.

Step 1: Start at one end of the scar. Place two Dolphin Neurostim devices ¼ inch to each side of one end of the scar (the devices will register the low frequency and identify this location). On one side the Dolphin Neurostim has a pre-selected negative (−ve) polarity, and on the other a positive/negative polarity (+/−). Which side on scar has (−ve) or (+/−ve) does not matter, only polarity of stimulation appears to matter. Both units are then simultaneously activated and held in place for 30 seconds. The two Dolphin Neurostim devices are then moved ¼" down the scar, held in place and then reactivated for another 30 second time frame. This process is repeated every ¼ inch along the entire length of the scar until applicator reaches the opposite end of scar to which they started.

Step 2: Place each device at opposite ends of the scar, one negative polarity (−ve) and the other positive/negative (+/−). Both units are then simultaneously activated and held in place for 30 seconds. If the scar ends are longer than ½ inch, then repeat above sequence at ¼ inch intervals. Palpate the texture of scar to determine degree of tissue release above steps provided.

Step 3: Place one unit (further called unit one) on acupuncture point B62 pre-set on a negative (−ve) polarity. B62 has been discovered to release fascial tension relating to scars, so this unit is held in place (static) for entire step 3. Unit two is placed directly on top of scar at one end preset on positive negative (+/−) polarity. Both devices are then simultaneously activated and held in pace for 30 seconds.

Step 4: Maintain above polarities for both devices. Keep Unit one on acupuncture point B62, and move unit two ¼ inch down the scar, and then simultaneously activate both devices for 30 seconds. Repeat above procedure every ¼ inch along entire length of scar.

Step 5: Place Unit one on acupuncture point St 36 negative (−ve) polarity, and maintain in place for entire step 5. This point releases internal adhesions relating to scars. Place device 2 (active device), above the scar at one end, one end preset on positive negative (+/−) polarity. Both devices are then simultaneously activated and held in pace for 30 seconds.

Step 6: Maintain above polarities for both devices. Keep Unit one on acupuncture point St36, and move unit two ¼ inch down the top side of the scar, and then simultaneously activate both devices for 30 seconds. Repeat above procedure every ¼ inch along entire length of top of scar.

Step 7: Place Unit one on acupuncture point Sp6 pre-set on a negative (−ve) polarity. Sp6 has been discovered to electrically reconnect the nervous system and increase cellular membrane deficiencies in scars. This unit is held in place (static) for entire step 7. Unit two is placed directly on top of scar at one end preset on negative (−) polarity. Both devices are then simultaneously activated and held in pace for 30 seconds.

Step 8: Maintain above polarities for both devices. Keep Unit one on acupuncture point Sp6, and move unit two ¼ inch down the scar, and then simultaneously activate both devices for 30 seconds. Repeat above procedure every ¼ inch along entire length of scar.

Step 9: To balance the autonomic nervous system after such a sympathetic release, the following two acupuncture points have been discovered to highly effective when treated with microcurrent. Gb 41 and H 7. Both are treated on negative (−ve) polarity and are a important step in ensuring a long term parasympathetic state.

Steps 10-22 are for emotional release relating to scars and trauma, such as PTSD. Each scar has a unique emotion associated with it, with some scars holding deep emotional trauma. In acupuncture, each organ has an associated emotion, and connecting key acupoints with scars for emotional release has proven to be significant advancement in the treatment of emotional related disease and pain.

Step 10: Place Unit one on acupuncture point H7 pre-set on a negative (−ve) polarity. H7 has been associated (connected) with emotion anxiety. This unit is held in place (static) for entire Step 10. Unit two is placed directly on top of scar at one end preset on negative (−) polarity. Both devices are then simultaneously activated and held in place for 30 seconds.

Step 11: Maintain above polarities for both devices. Keep Unit one on acupuncture point H7, and move unit two ¼ inch down the scar, and then simultaneously activate both devices for 30 seconds. Repeat above procedure every ¼ inch along entire length of scar.

Step 12: Place Unit one on acupuncture point Lu7 pre-set on a negative (−ve) polarity. Lu7 has been associated (connected) with emotion grief. This unit is held in place (static) for entire step 10. Unit two is placed directly on top of scar at one end preset on negative (−) polarity. Both devices are then simultaneously activated and held in pace for 30 seconds.

Step 13: Maintain above polarities for both devices. Keep Unit one on acupuncture point Lu7, and move unit two ¼ inch down the scar, and then simultaneously activate both devices for 30 seconds. Repeat above procedure every ¼ inch along entire length of scar.

Step 14: Place Unit one on acupuncture point P6 pre-set on a negative (−ve) polarity. P6 has been associated (connected) with emotion broken heart. This unit is held in place (static) for entire step 12. Unit two is placed directly on top of scar at one end preset on negative (−) polarity. Both devices are then simultaneously activated and held in pace for 30 seconds.

Step 15 Maintain above polarities for both devices. Keep Unit one on acupuncture point P6, and move unit two, ¼ inch down the scar, and then simultaneously activate both devices for 30 seconds. Repeat above procedure every ¼ inch along entire length of scar.

Step 16: Place Unit one on acupuncture point Liv 3 pre-set on a negative (−ve) polarity. Liv 3 has been associated (connected) with emotion anger. This unit is held in place (static) for entire step 14. Unit two is placed directly on top of scar at one end preset on negative (−) polarity. Both devices are then simultaneously activated and held in pace for 30 seconds.

Step 17: Maintain above polarities for both devices. Keep Unit one on acupuncture point Liv 3, and move unit two ¼ inch down the scar, and then simultaneously activate both devices for 30 seconds. Repeat above procedure every ¼ inch along entire length of scar.

Step 18: Place Unit one on acupuncture point K3 pre-set on a negative (−ve) polarity. K3 has been associated (connected) with emotion fear. This unit is held in place (static) for entire step 16. The 2nd Unit two is placed directly on top of scar at one end preset on negative (−) polarity. Both devices are then simultaneously activated and held in pace for 30 seconds.

Step 19: Maintain above polarities for both devices. Keep Unit one on acupuncture point K3, and move unit two ¼ inch down the scar, and then simultaneously activate both devices for 30 seconds. Repeat above procedure every ¼ inch along entire length of scar.

Step 20: Place Unit one on acupuncture point Sp6 pre-set on a negative (−ve) polarity. Sp6 has been associated (connected) with emotion worry. This unit is held in place (static) for entire step 8. Unit two is placed directly on top of scar at one end preset on negative (−) polarity. Both devices are then simultaneously activated and held in pace for 30 seconds.

Step 21: Maintain above polarities for both devices. Keep unit one on acupuncture point Sp6, and move unit two ¼ inch down the scar, and ten simultaneously activate both devices for 30 seconds. Repeat above procedure every ¼ inch along entire length (or circumference) of scar.

Step 22: To balance the autonomic nervous system after such a sympathetic release, the following 2 acupuncture points have been discovered to highly effective when treated with microcurrent. Gb 41 and H 7. Both are treated on negative (−ve) polarity and are a critical step in ensuring a long term parasympathetic state.

Step 23-29 are for Internal Adhesion Release. If this step is included with any previous treatment steps, then repeat step 22—Balance of the Autonomic Nervous System, again AFTER step 27. There are 5 points used for Internal Adhesion Release (IAR-MPS Method). Gv 4, and both B25 and Gb 12 points.

Gv 4 represents Kidney elimination and "gate of Life", B25 represents large Intestine elimination and GB 12 influences the vagus nerve and reduces vagal tone.

Step 23: For this step, place Unit one on Gv4 (+/−). This unit is held in place (static) for entire step 23. Unit two is placed directly on top of abdominal scar at one end preset on negative (−) polarity. Both devices are then simultaneously activated and held in pace for 30 seconds.

Step 24: Maintain above polarities for both devices. Keep unit one on acupuncture point GV 4, and move unit two, ¼ inch down the scar, and then simultaneously activate both devices for 30 seconds. Repeat above procedure every ¼ inch along entire outside circumference of scar.

Step 25: For this step, place Unit one on either B 25 (+/−). This unit is held in place (static) for entire step 25. Unit two is placed directly on top of abdominal scar at one end preset on negative (−) polarity. Both devices are then simultaneously activated and held in pace for 30 seconds.

Step 26: Maintain above polarities for both devices. Keep unit one on the second acupuncture point B25, and move unit two, ¼ inch down the scar, and then simultaneously activate both devices for 30 seconds. Repeat above procedure every ¼ inch along entire outside circumference of scar.

Step 27: For this step, place Unit one on either Gb 12 (+/−). This unit is held in place (static) for entire step 27. Unit two is placed on the abdominal scar at one end preset on negative (−) polarity. Both devices are then simultaneously activated and held in pace for 30 seconds.

Step 28: Maintain above polarities for both devices. Keep unit one on the second acupuncture point Gb 12, and move unit two, ¼ inch down the scar, and then simultaneously activate both devices for 30 seconds. Repeat above procedure every ¼ inch along entire outside circumference of scar while maintaining static application of Gb 12.

Step 29: To balance the patients autonomic nervous system after sympathetic deregulation, the following two acupuncture points, Gb 41 and H 7, were discovered to highly effective when treated with MPS microcurrent. Both are treated on negative (−ve) polarity and are a important step in ensuring a long term autonomic nervous system balance.

It should be noted that in the above steps and elsewhere, the term "on the scar" means directly on the scar tissue itself or on non-scar tissue very near the scar tissue itself. In particular, it can mean slightly above or below the scar tissue.

It should also be noted that many acupuncture points appear on both sides of the body, such as for point H7 which appears on the left wrist and the right wrist. The terms Left H7 and Right H7 may be used for all such bilateral acupuncture points. Left and right are determined from the perspective of the patient.

Figure 1:
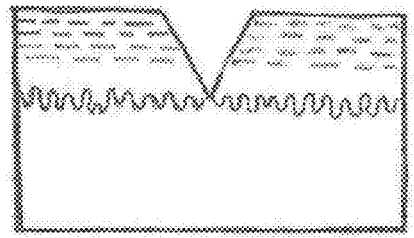
Figure 1:
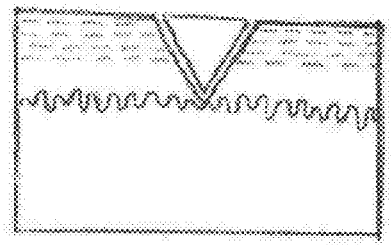
Figure 1:
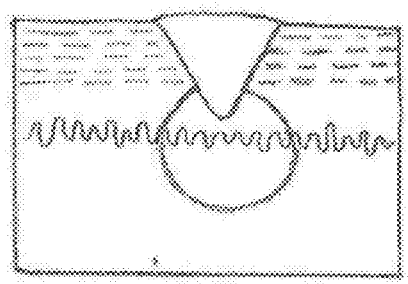
Figure 1:
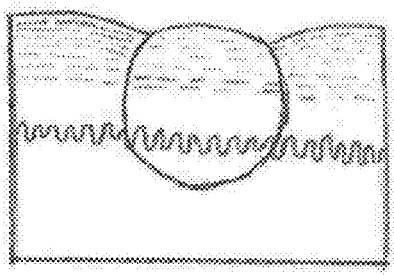

Turning to the figures:

FIG. 1 illustrates a cross section of the Four Stages of Scar Formation; injury/cut, blood clot, scab and scar formation.

Figure 2:
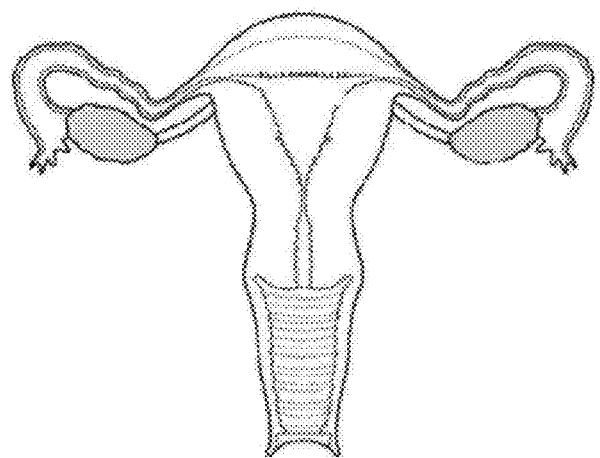
Figure 2:
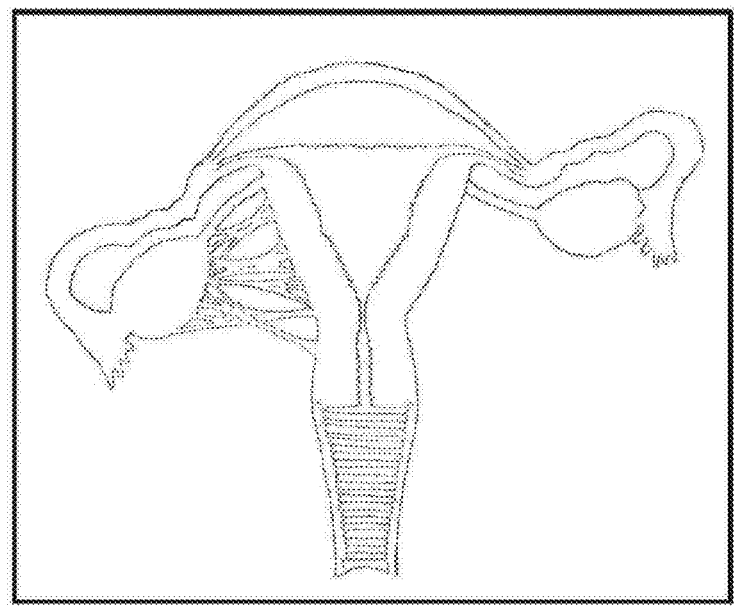

FIG. 2 illustrates a uterus with no adhesions and a uterus with adhesions.

Figure 3:
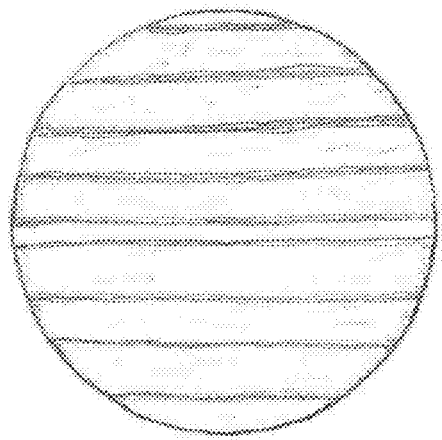
Figure 3:
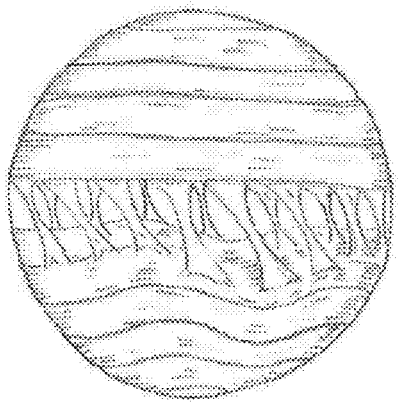

FIG. 3 illustrates muscle fibres with no adhesions and muscle fibres with adhesions.

Figure 4:
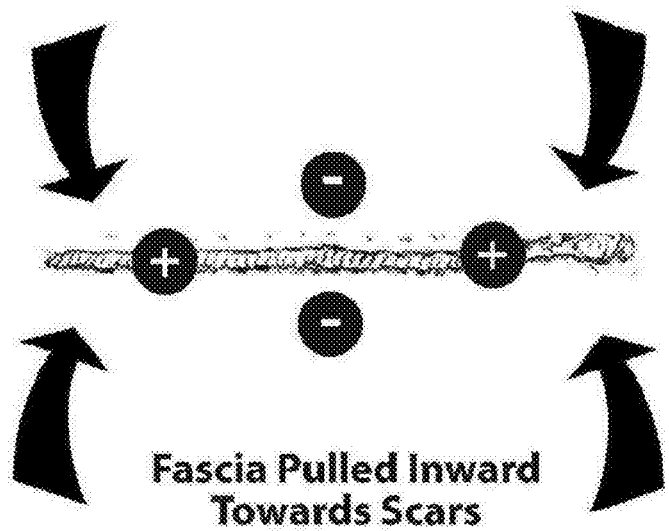

FIG. 4 illustrates a View of being fascia pulling inwards towards a scar and the resulting electrical polarity changes of the scar and surrounding tissues left after scar formation.

Figure 5:
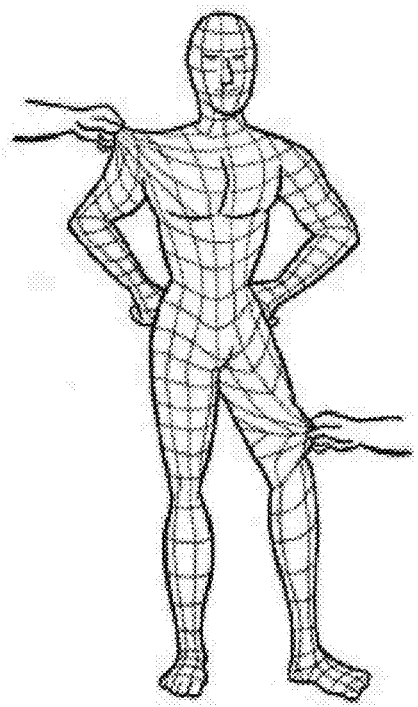

FIG. 5 illustrates a View of the Body-wide Fascia system being strained from being pulled at the right shoulder and left knee.

Figure 6:
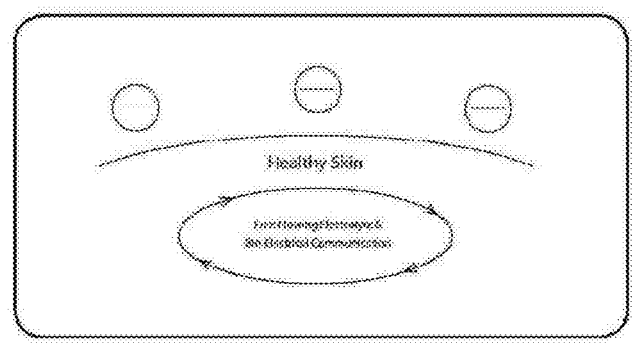

FIG. 6 illustrates a View Electrical Polarity of Normal Skin and the free flowing of electrolytes and bio-electrical communications.

Figure 7:
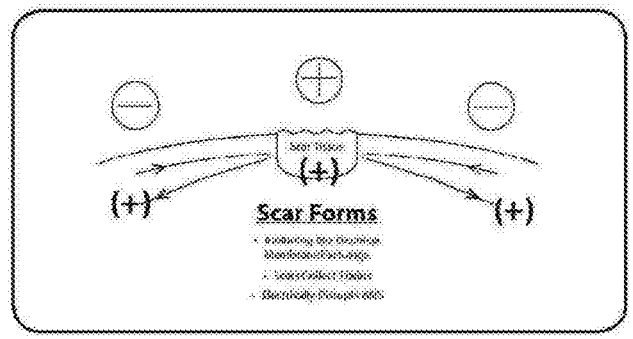

FIG. 7 illustrates a View of the Electrical Polarity of Skin and Scars after Scar. formation and the resulting inhibition of bio-electrical membranes exchange, collection of cellular toxins and electrical disruption of the autonomic nervous system.

Figure 8:
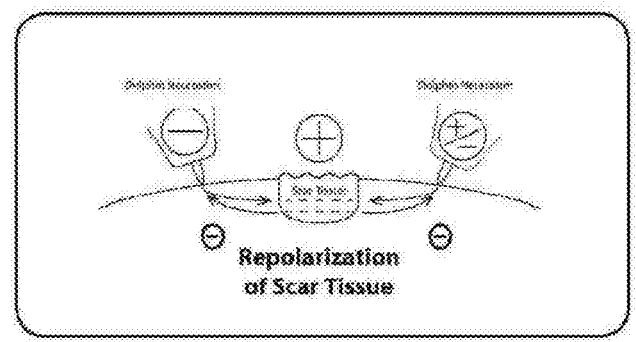

FIG. 8 illustrates a View of the Electrical Polarity of current flowing through scar tissue during SRT-MPS Method application and the subsequent repolarization of scar tissue.

Figure 9:
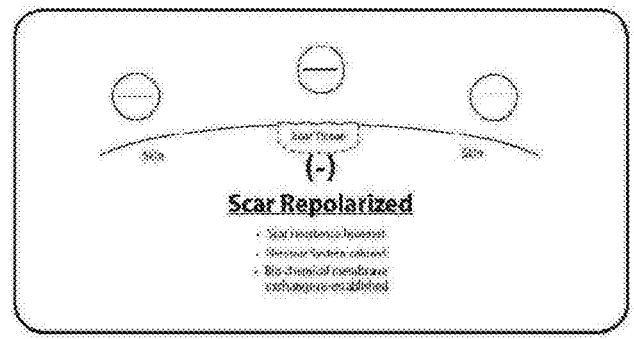

FIG. 9 illustrates a View of the Electrical Polarity of Skin and Scars after SRT-MPS Method application, with scar resistance lowered, sympathetic nervous system tone reduced and the re-establishments of bio-chemical membrane exchange.

Figure 10:
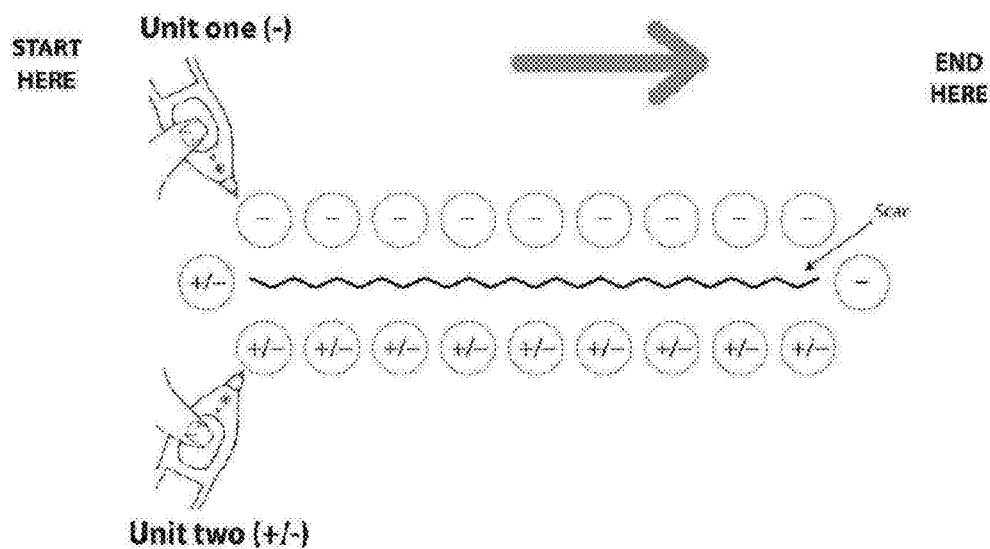

FIG. 10 illustrates a top view of the methodology placement and polarity settings of unit one and unit two during Scar Release Therapy-MPS Method.

Figure 11:
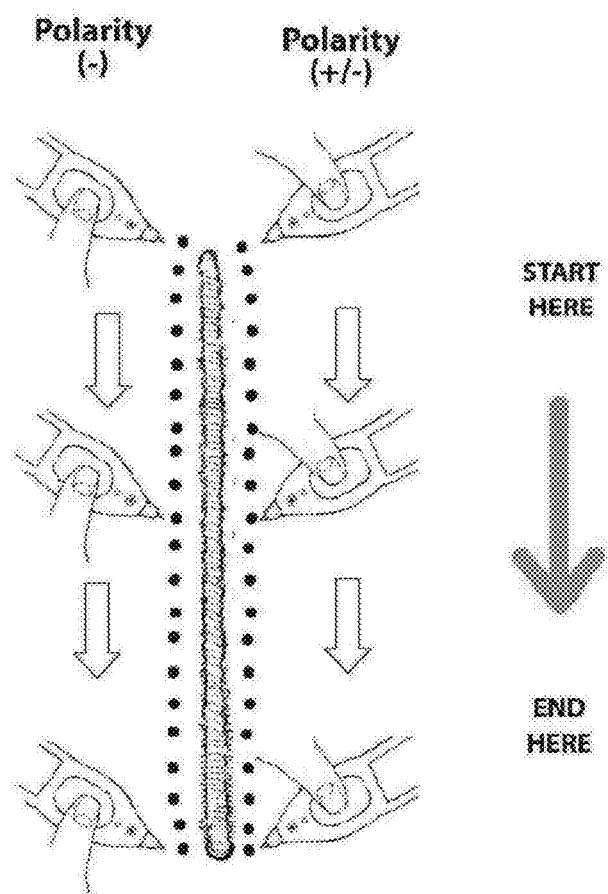

FIG. 11 illustrates a top view of the direction of application methodology and electrical polarity of unit one and unit two devices during SRT-MPS para-scar treatment.

Figure 12:
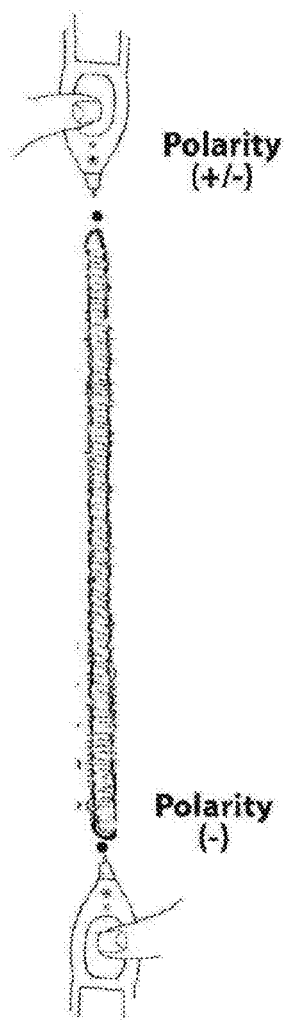

FIG. 12 illustrates a top view of the application methodology and electrical polarity of devices during SRT-MPS opposite end treatment.

Figure 13:
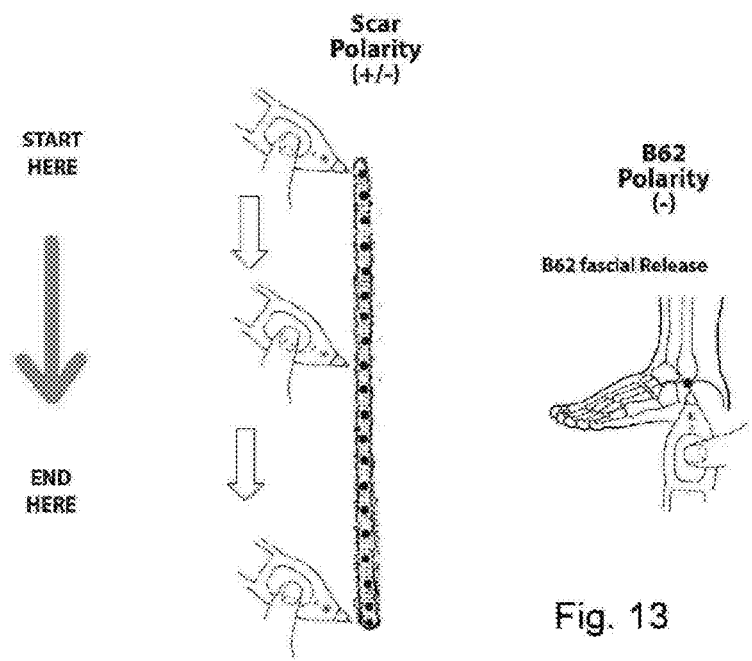

FIG. 13 illustrates a view of acupuncture point B 62 and the methodology placement and polarity settings of unit one and unit two during Fascia Release-SRT MPS Method.

Figure 14:
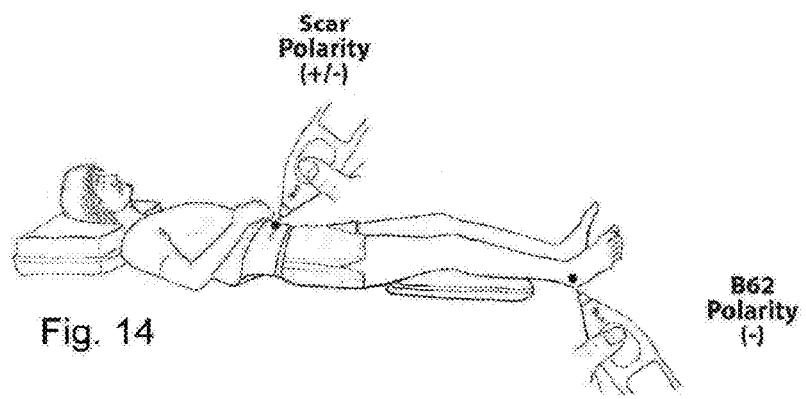

FIG. 14 illustrates a side view of patient positioning, electrical polarity and position of unit one, placed on the scar, and unit two, placed on B62, during Fascia Release-SRT MPS Method.

Figure 15:
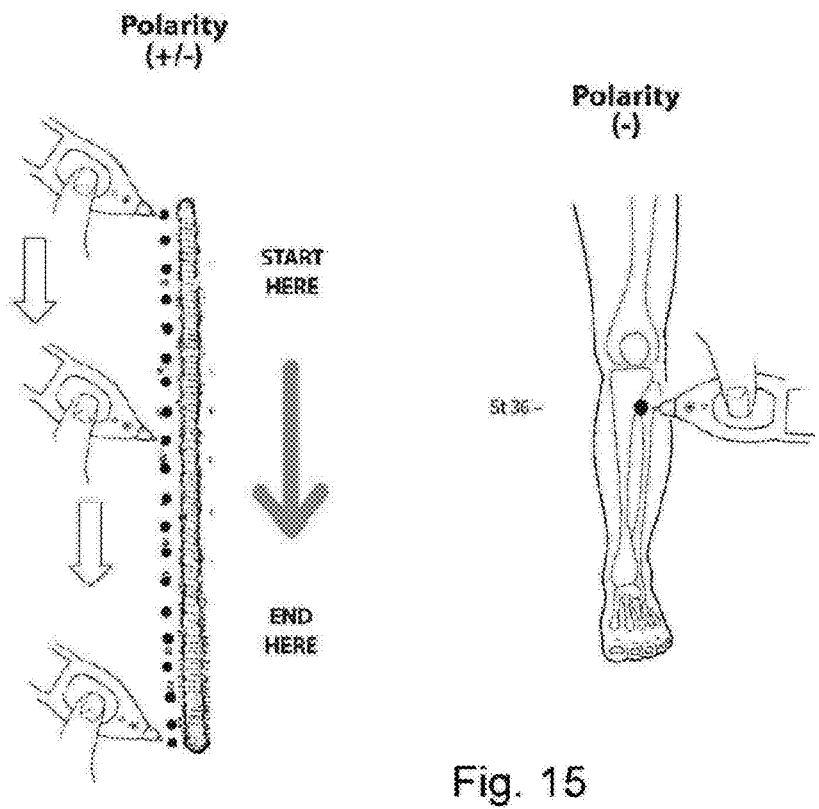

FIG. 15 illustrates a view of acupuncture point St36 and the methodology placement and polarity settings of unit one and unit two during Adhesion Release-SRT MPS Method.

Figure 16:
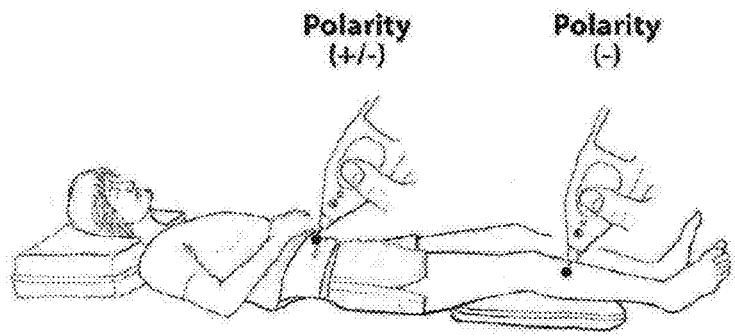

FIG. 16 illustrates a side view of patient positioning, electrical polarity and placement of unit one placed on the scar, and unit two, placed on St 36, during Adhesion Release-SRT MPS Method.

Figure 17:
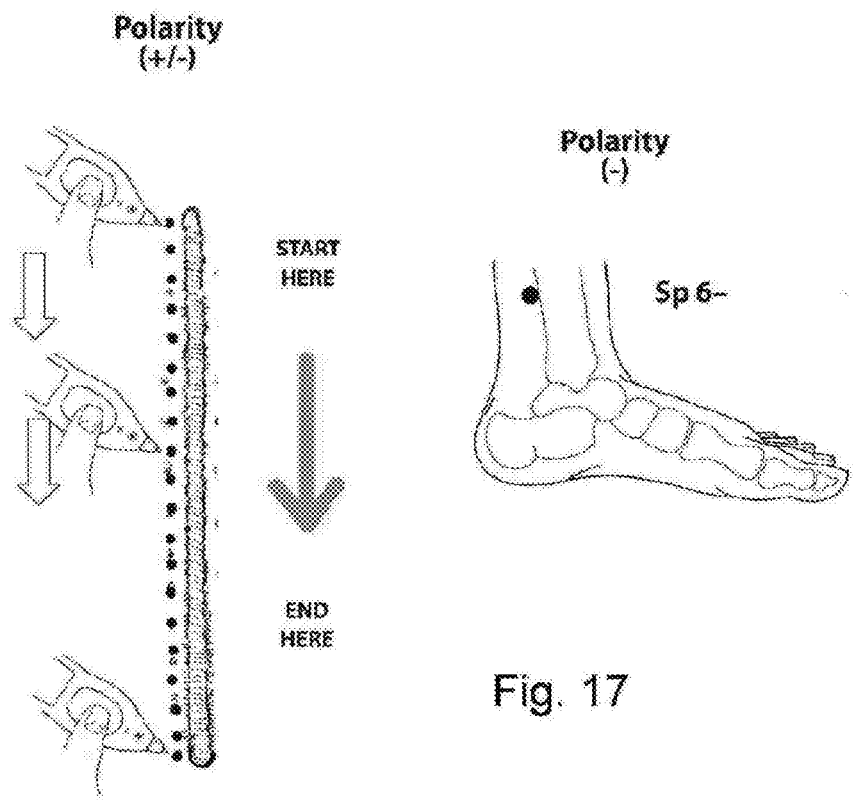

FIG. 17 illustrates a view of acupuncture point Sp 6 and the methodology placement and polarity settings of unit one and unit two during Electrical Reconnection-SRT MPS Method.

Figure 18:
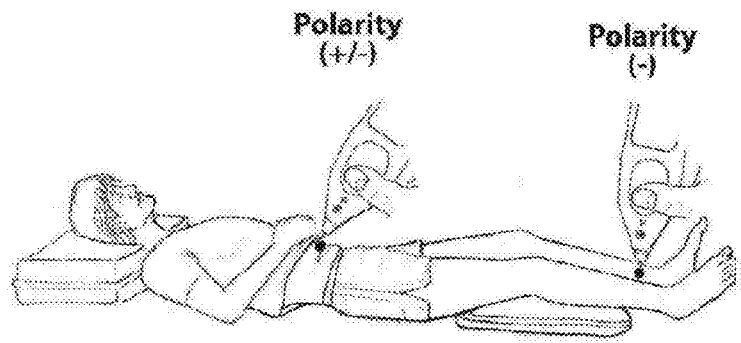

FIG. 18 illustrates a side view of acupuncture point Sp 6 and the patient positioning, electrical polarity and placement of unit one and unit two during Electrical Reconnection-SRT MPS Method.

Figure 19:
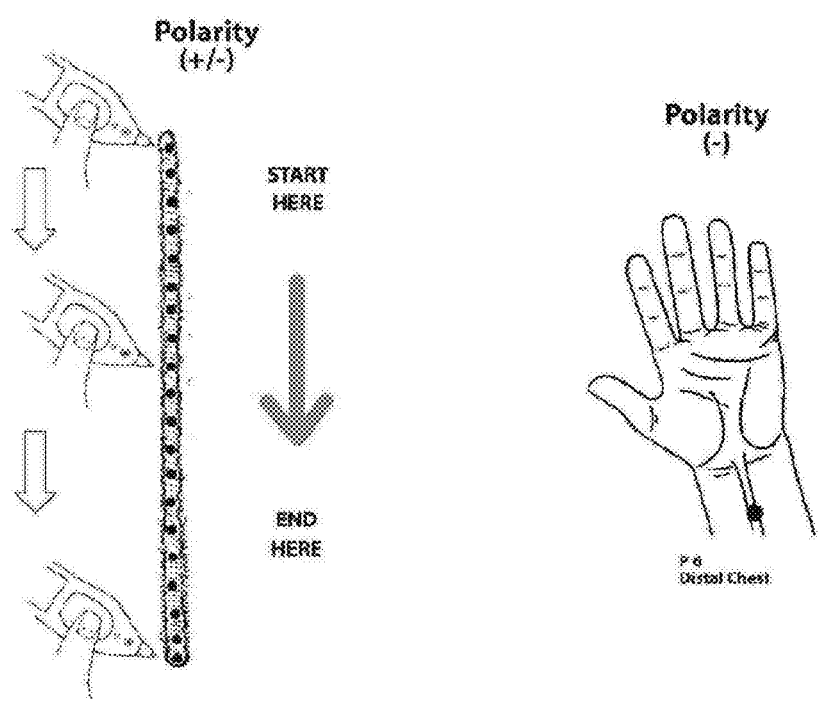

FIG. 19 illustrates a view of acupuncture point P6 and the application methodology and electrical polarity of unit one and unit two devices during Emotional Broken Heart Release-SRT MPS Method.

Figure 20:
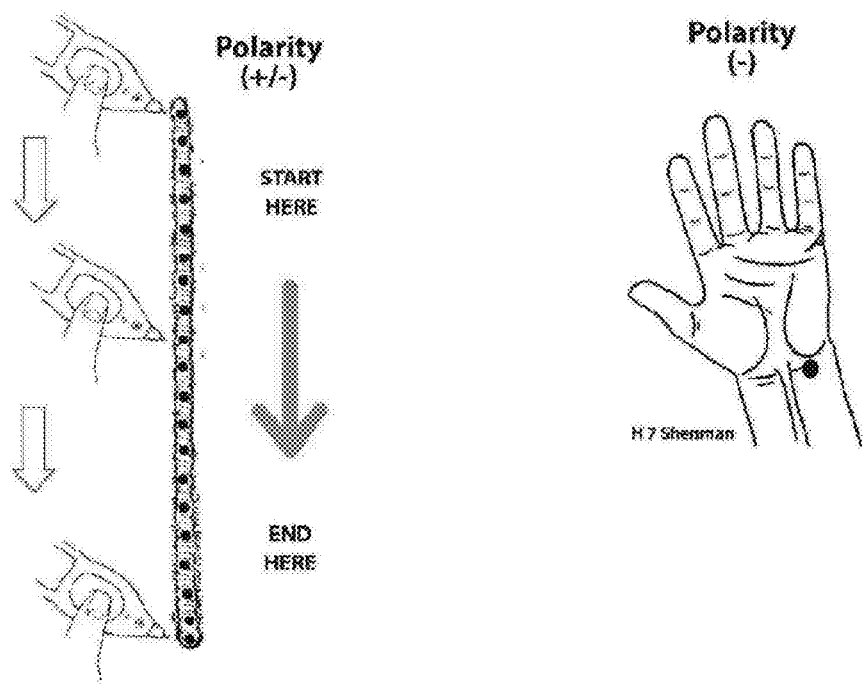

FIG. 20 illustrates a view of acupuncture point H7 and the application methodology and electrical polarity of unit one and unit two devices during Emotional Anxiety Release-SRT MPS Method.

Figure 21:
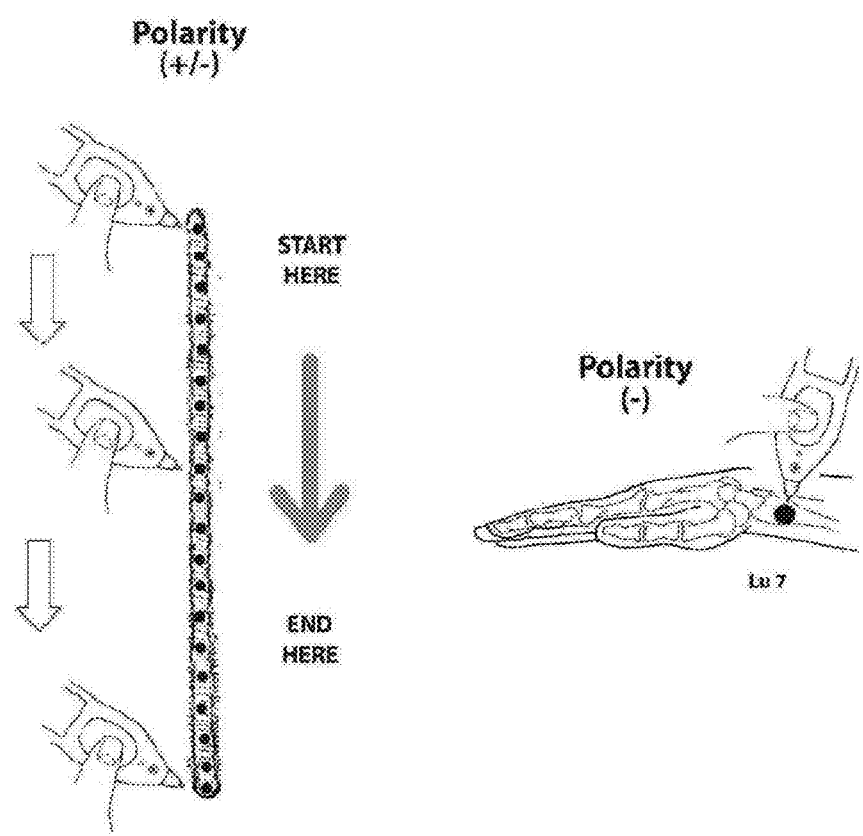

FIG. 21 illustrates a view of acupuncture point Lu7 and the application methodology and electrical polarity of unit one and unit two devices during Emotional Grief Release-SRT MPS Method.

Figure 22:
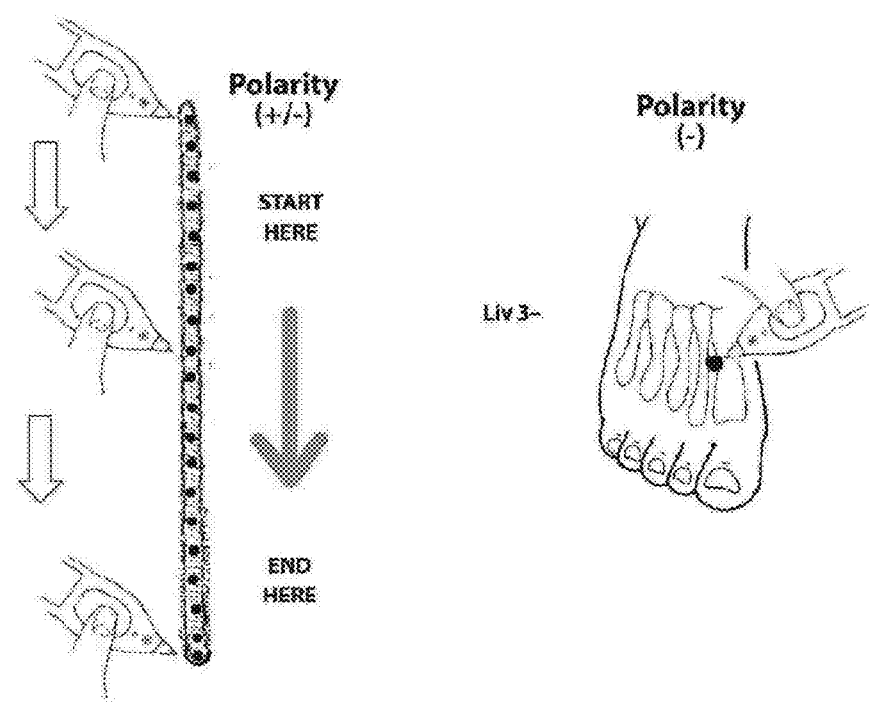

FIG. 22 illustrates a view of acupuncture point Liv 3 and the application methodology and electrical polarity of unit one and unit two devices during Emotional Anger Release-SRT MPS Method.

Figure 23:
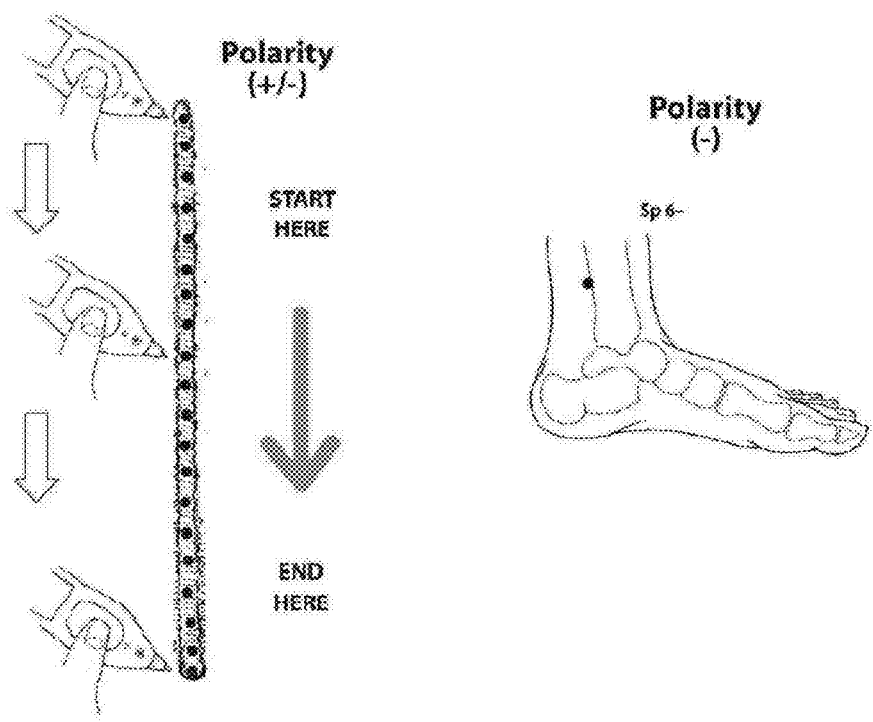

FIG. 23 illustrates a view of acupuncture point Sp6 and the application methodology and electrical polarity of unit one and unit two devices during Emotional Worry Release-SRT MPS Method.

Figure 24:
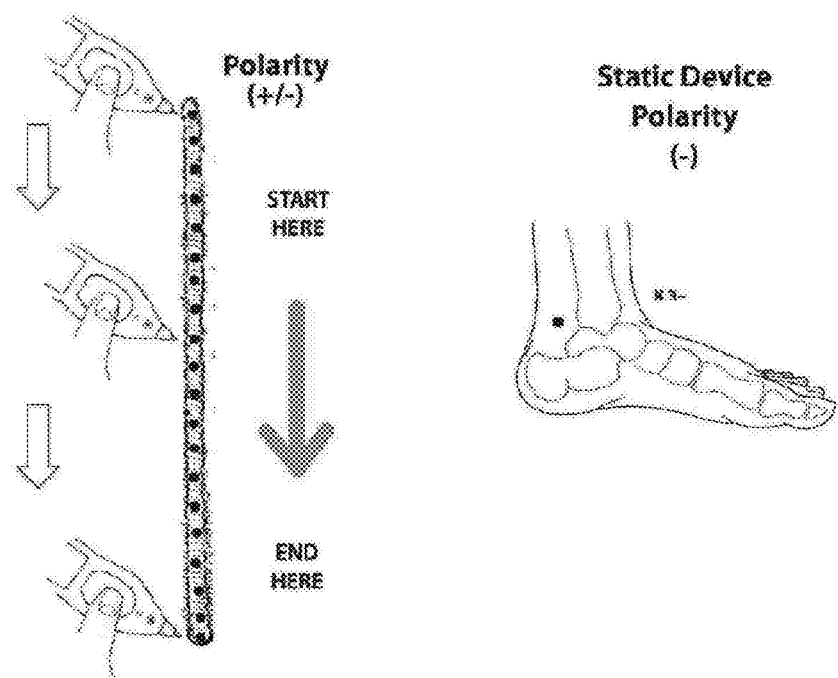

FIG. 24 illustrates a view of acupuncture point K3 and the application methodology and electrical polarity of unit one and unit two devices during Emotional Fear Release-SRT MPS Method.

Figure 25:
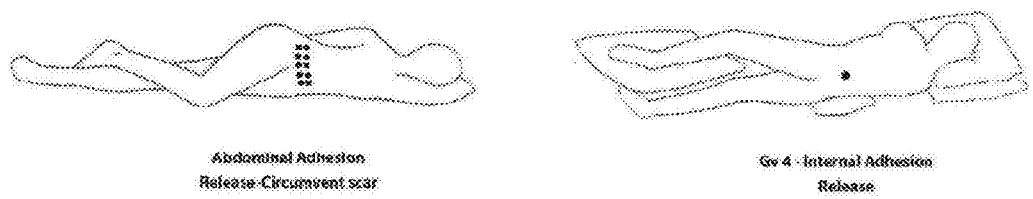
Figure 25:
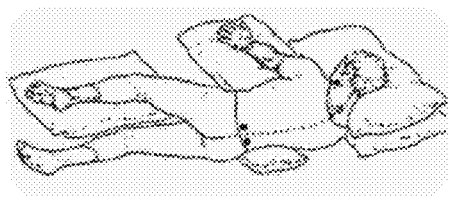

FIG. 25 illustrates patient positioning, and location of acupuncture points Gv4 and B25 for Internal Adhesion Release-MPS Method.

FIG. 26 illustrates a view of acupuncture point Gv 4 and the methodology placement and polarity settings of unit one and unit two during Internal Adhesions Release-SRT MPS Method.

FIG. 27 illustrates a view of acupuncture point B25 and the application methodology and electrical polarity of unit one and unit two devices during Internal Adhesions Release-SRT MPS Method.

Figure 28:
Figure 28:
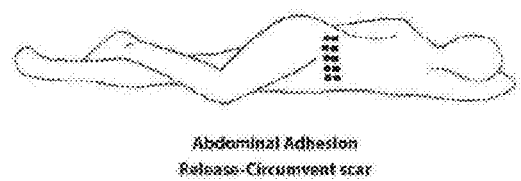

FIG. 28 illustrates a view of acupuncture point Gb 12 and the placement and polarity settings of unit one and unit two during for Vagus Nerve Release-MPS Method.

Figure 29:
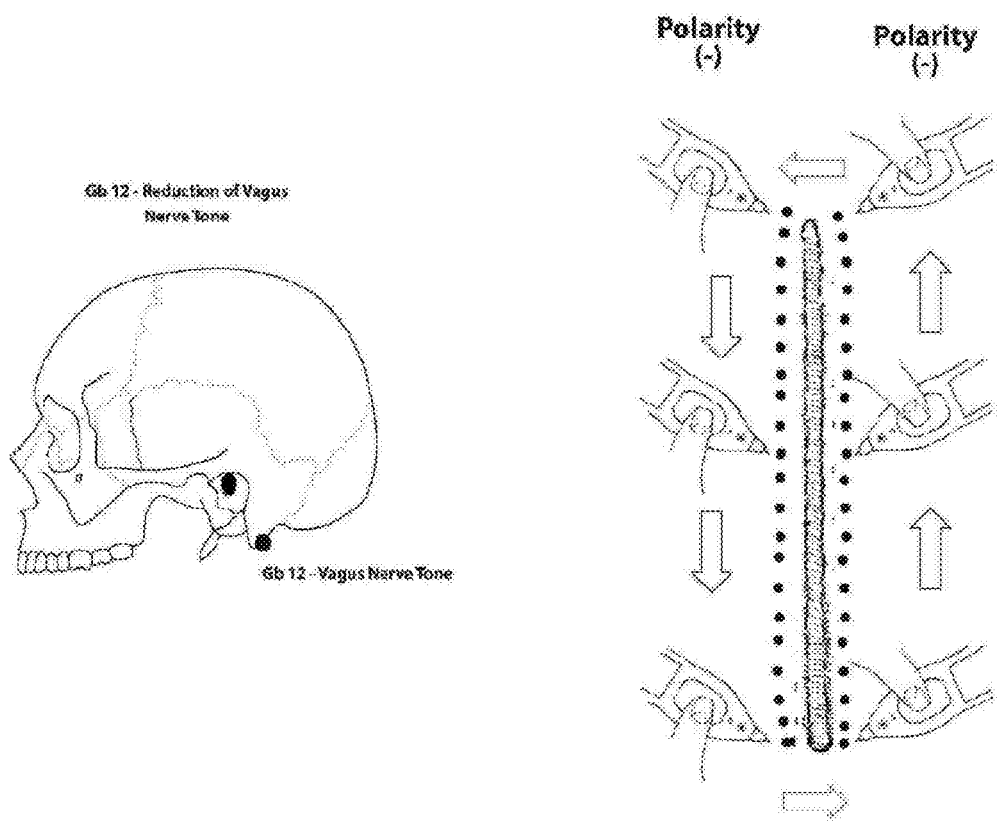

FIG. 29 illustrates a view of acupuncture point Gb 12 and the application methodology and electrical polarity of unit one and unit two devices during Vagus Nerve Release-MPS Method.

Figure 30:
Figure 31:
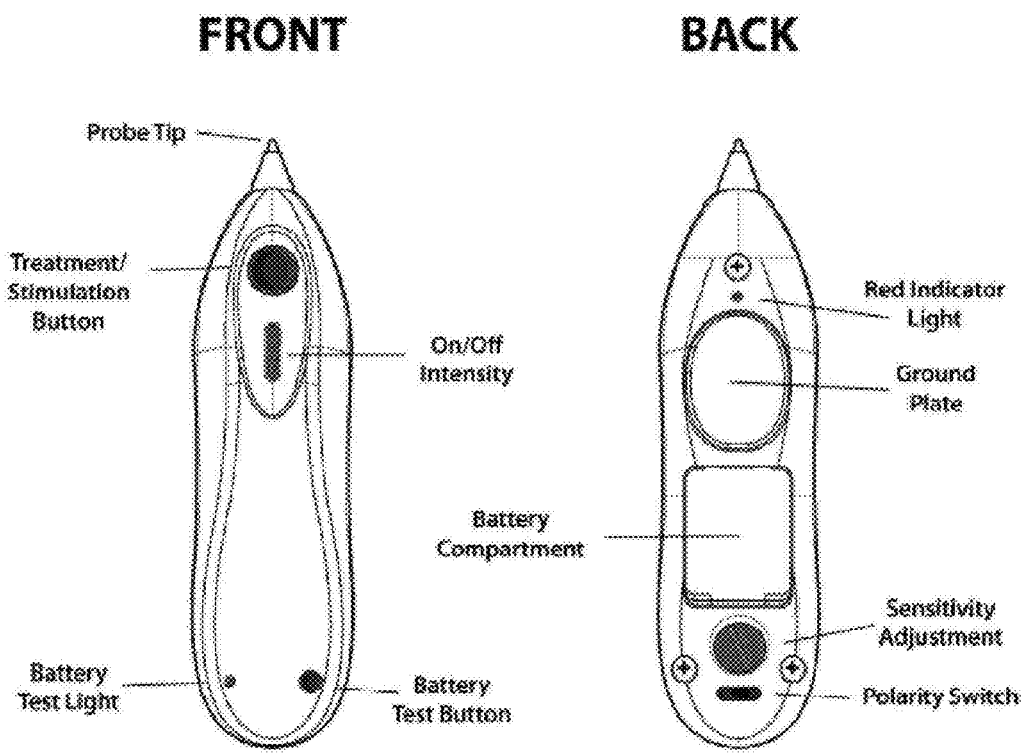

FIG. 30 illustrates a view of acupuncture points H 7 and Gb 41 and the electrical polarity of devices one and two during Autonomic Nervous System balance-SRT MPS Method.

FIG. 32 illustrates the front and back views of the present invention therapeutic device and describes the device features and polarity settings.

Several descriptions and illustrations have been presented to aid in understanding the present invention. One with skill in the art will realize that numerous changes and variations may be made without departing from the spirit of the invention. Each of these changes and variations is within the scope of the present invention.

I claim:

1. A method using two electronic microcurrent injection devices in a mirrored relationship to electrically repolarize positively poled scar tissue with negatively poled electrical microcurrent in order to produce bio-cellular change to the scar and adhesive tissue for rehabilitation of scar tissue comprising the following steps taken in order:

(a) starting at a first end of a scar, placing tips of a first and a second electronic microcurrent injection device ¼ inch to each side of one end of a scar, the first electronic microcurrent injection device injecting a negative polarity DC electrical microcurrent through its tip; the second electronic microcurrent injection device injecting a positive/negative polarity pulsed square wave electrical microcurrent through its tip; the first and second devices acting in a mirror relationship causing a negative poled electrical microcurrent to flow back and forth between the devices causing cellular repolarization from positive to negative polarization;

(b) injecting the electrical microcurrent between the devices causing cellular repolarization by holding both units devices in place for 30 seconds;

(c) moving both devices ¼" down the scar;

(d) repeating steps (b) and (c) until a second end of the scar is reached.

2. The method of claim 1 further comprising the following additional steps taken in order:

placing each device at opposite ends of the scar, ene the first device set to inject current of negative polarity and the other device set to inject pulsed current of positive/negative polarity;

injecting the electrical microcurrent between the devices causing cellular repolarization by simultaneously activating both devices and holding them in place for 30 seconds.

3. The method of claim 2 further comprising the following steps executed in order:

(e) placing the first device on acupuncture point B62 set to inject current of negative polarity;

(f) placing the second device directly on top of the scar at one end set to inject pulsed current of positive negative (+/−) polarity;

(g) injecting the electrical microcurrent between the two devices causing cellular repolarization by activating and holding both devices in place for 30 seconds, then deactivating both devices;

(h) moving the second device ¼ inch down the scar;

(i) repeating steps (g) and (h) until a second end of the scar is reached.

4. The method of claim 3 further comprising the following steps executed in order:

placing the second device on the scar at one end still set to inject pulsed current of positive/negative (+/−) polarity;

repeating the steps of claim 3 with the first device on acupuncture point St 36 still set to inject current of negative polarity.

5. The method of claim 4 further comprising the following steps executed in order:

placing the second device on the scar at one end still set to inject current of positive negative (+/−) polarity;

repeating the steps of claim 3 with the first unit on acupuncture point Sp 6 still set to inject current of negative polarity.

6. The method of claim 5 further comprising the steps executed in order:

placing the first device on acupuncture point GV 20 and the second device on acupuncture point Left H7 with the first and second devices set to inject current of negative polarity;

injecting the electrical microcurrent between the two devices causing cellular repolarizaion by activating both devices for 30 seconds;

deactivating both devices;

placing the second device on acupuncture point Right H7 still set to inject current of negative polarity;

injecting the electrical microcurrent between the two devices causing cellular repolarization by activating both devices for 30 seconds;

deactivating both devices.

7. The method of claim 6 further comprising the following steps executed in order:

repeating steps (f), (g), (h) and (i) of claim 3 with the first unit device on acupuncture point H7 set to inject current of negative polarity;

repeating steps (f), (g), (h) and (i) of claim 3 with the device on acupuncture point Lu7 set to inject current of negative polarity;

repeating steps (f), (g), (h) and (i) of claim 3 with the device on acupuncture point P6 set to inject current of a negative polarity;

repeating steps (f), (g), (h) and (i) of claim 3 with the device on acupuncture point Liv3 set to inject current of a negative polarity;

repeating steps (f), (g), (h) and (i) of claim 3 with the device on acupuncture point K3 set to inject current of a negative polarity;

repeating steps (f), (g), (h) and (i) of claim 3 with the device on acupuncture point Sp6 set to inject current of a negative polarity.

8. The method of claim 7 further comprising the following steps executed in order:

repeating steps (f), (g), (h) and (i) of claim 3 with the first unit on acupuncture point Gv4 set to inject current of a negative polarity;

repeating steps (f), (g), (h) and (i) of claim 3 with the first unit on acupuncture point B 25 set to inject current of a negative polarity;

repeating steps (f), (g), (h) and (i) of claim 3 with the first unit on acupuncture point Gb 12 set to inject current of a negative polarity.

9. The method of claim 1 further comprising the following additional steps taken in order:

(e) placing the first device on acupuncture point B62 pre-set to inject current of negative polarity;

(f) placing the second device directly on top of the scar at one end set to inject pulsed current of positive negative (+/−) polarity;

(g) injecting the electrical microcurrent between the devices causing cellular repolarization by activating both devices and holding both devices in place for 30 seconds, then deactivating both devices;

(h) moving the second device ¼ inch down the scar;

(i) repeating steps (g) and (h) until a second end of the scar is reached.

10. The method of claim 9 further comprising the following additional steps taken in order:

placing the second device on the scar at one end still set to inject pulsed current of positive/negative (+/−) polarity;

repeating the steps of claim 9 with the first device on acupuncture point St 36 still set to inject current of negative polarity.

11. The method of claim 9 further comprising the following additional steps taken in order:

placing the second device on the scar at one end still set to inject current of positive negative (+/−) polarity;

repeating the steps of claim 9 with the first unit on acupuncture point Sp 6 still set to inject current of negative polarity.

12. The method of claim 9 further comprising the following additional steps taken in order:

placing the first device on acupuncture point GV 20 and the second device on acupuncture point Left H7 with the first and second devices set to inject current of negative polarity;

injecting the electrical microcurrent between the two devices causing cellular repolarization by activating both devices for 30 seconds;

deactivating both devices;

placing the second device on acupuncture point Right H7 still set to A inject current of negative polarity;

injecting the electrical microcurrent between the two devices causing cellular repolarization by activating both devices for 30 seconds;

deactivating both devices.

13. A method using two electronic microcurrent injection devices in a mirrored relationship to electrically repolarize positively poled scar tissue with negatively poled electrical microcurrent in order to produce bio-cellular change to the scar and adhesive tissue for rehabilitation of scar tissue comprising the following steps taken in order:

(a) starting at a first end of a scar, placing tips of a first and a second electronic microcurrent injection device tip ¼ inch to each side of one end of a scar, the first electronic microcurrent injection device injecting a negative polarity DC electrical microcurrent through its tip; the second electronic microcurrent injection device injecting a positive/negative polarity pulsed square wave electrical microcurrent through its tip; the first and second devices acting in a mirror relationship causing a negative poled electrical microcurrent to flow back and forth between the devices causing cellular re-polarization from positive to negative polarization;

(b) injecting the electrical microcurrent between the two devices causing cellular repolarization by activating both devices and holding both units devices in place for 30 seconds;

(c) moving both units devices ¼" down the scar;

(d) repeating steps (b) and (c) until a second end of the scar is reached;

(e) placing each device at opposite ends of the scar, one the first device set to inject current of negative polarity and the other device set to inject pulsed current of positive/negative polarity;

(f) injecting the electrical microcurrent between the two devices causing cellular repolarization by simultaneously activating both units devices and holding them in place for 30 seconds;

(g) placing the first device on acupuncture point B62 set to inject current of negative polarity;

(h) placing the second device directly on top of the scar at one end set to inject pulsed current of positive negative (+/−) polarity;

(i) injecting the electrical microcurrent between the two devices causing cellular repolarization by activating and holding both devices in place for 30 seconds, then deactivating both devices;

(j) moving the second device ¼ inch down the scar;

(k) repeating steps (g) and (h) until a second end of the scar is reached.

14. The method of claim 13 further comprising:

repeating the steps (h), (i), (j) and (k) with the first device on acupuncture point St 36 set to inject current with a negative polarity.

15. The method of claim 13 further comprising:

repeating the steps (h), (i), (j) and (k) with the first device on acupuncture point Sp6 set to inject current with a negative polarity.

16. The method of claim 13 further comprising the following additional steps performed in order:

placing the first device on acupuncture point GV 20 and the second device on acupuncture point Left H7 with the first and second devices set to inject current of negative polarity;

injecting the electrical microcurrent between the two devices causing cellular repolarization by activating both devices for 30 seconds;

deactivating both devices;

placing the second device on acupuncture point Right H7 still set to inject current of negative polarity;

injecting the electrical microcurrent between the two devices causing cellular repolarization by activating both devices for 30 seconds;

deactivating both devices.

17. The method of claim 13 further comprising:

repeating the steps (h), (i), (j) and (k) with the first unit on acupuncture point H7 set to inject current with a negative polarity;

repeating the steps (h), (i), (j) and (k) with the first unit on acupuncture point Lu7 set to inject current with a negative polarity;

repeating the steps (h), (i), (j) and (k) with the first unit on acupuncture point P6 set to inject current with a negative polarity;

repeating the steps (h), (i), (j) and (k) with the first unit on acupuncture point Sp6 set to inject current with a negative polarity;

repeating the steps (h), (i), (j) and (k) with the first unit on acupuncture point K3 set to inject current with a negative polarity;

repeating the steps (h), (i), (j) and (k) with the first unit on acupuncture point Liv 3 set to inject current with a negative polarity.

18. The method of claim 13 further comprising repeating the steps (h), (i), (j) and (k) with the first unit on acupuncture point Gv4 set to inject current with a negative polarity;

repeating the steps (h), (i), (j) and (k) with the first unit on acupuncture point B 25 set to inject current with a negative polarity;

repeating the steps (h), (i), (j) and (k) with the first unit on acupuncture point Gb 12 set to inject current with a negative polarity.

\* \* \* \* \*